United States Patent
Ko et al.

(10) Patent No.: US 11,053,184 B2
(45) Date of Patent: Jul. 6, 2021

(54) DOWNSTREAM PROCESSING OF FATTY ALCOHOL COMPOSITIONS PRODUCED BY RECOMBINANT HOST CELLS

(71) Applicant: GENOMATICA, INC., San Diego, CA (US)

(72) Inventors: Myong K. Ko, South San Francisco, CA (US); Haibo Wang, South San Francisco, CA (US); Patricia J. Cole, South San Francisco, CA (US); Perry Y. Liao, South San Francisco, CA (US); Simon Li, South San Francisco, CA (US)

(73) Assignee: GENOMATICA, INC., San Diego, CA (US)

( * ) Notice: Subject to any disclaimer, the term of this patent is extended or adjusted under 35 U.S.C. 154(b) by 303 days.

(21) Appl. No.: 14/773,149

(22) PCT Filed: Mar. 7, 2014

(86) PCT No.: PCT/US2014/021776
§ 371 (c)(1),
(2) Date: Sep. 4, 2015

(87) PCT Pub. No.: WO2014/138590
PCT Pub. Date: Sep. 12, 2014

(65) Prior Publication Data
US 2016/0009617 A1    Jan. 14, 2016

Related U.S. Application Data

(60) Provisional application No. 61/774,375, filed on Mar. 7, 2013.

(51) Int. Cl.
*C07C 29/88* (2006.01)
*C07C 29/17* (2006.01)

(52) U.S. Cl.
CPC ............ *C07C 29/88* (2013.01); *C07C 29/172* (2013.01)

(58) Field of Classification Search
None
See application file for complete search history.

(56) References Cited

U.S. PATENT DOCUMENTS

| | | | |
|---|---|---|---|
| 2,753,297 | A | 7/1956 | Mason et al. |
| 5,069,829 | A | 12/1991 | Van Dalen et al. |
| 6,855,851 | B2 | 2/2005 | Zgorzelski |
| 2010/0105963 | A1 | 4/2010 | Hu |
| 2011/0250663 | A1 | 10/2011 | Schirmer et al. |
| 2011/0256599 | A1 | 10/2011 | Hu et al. |
| 2012/0083631 | A1 | 4/2012 | Mirk et al. |
| 2012/0142979 | A1 | 6/2012 | Keasling et al. |
| 2012/0203018 | A1 | 8/2012 | Franklin et al. |

FOREIGN PATENT DOCUMENTS

| | | |
|---|---|---|
| AU | 2014225436 B2 | 9/2015 |
| CA | 1334420 | 2/1995 |
| EP | 0 389 057 | 9/1990 |
| EP | 2 522 650 | 11/2012 |
| EP | 2522650 A1 | 11/2012 |
| JP | 59-118090 | 7/1984 |
| JP | S59-118090 | 7/1984 |
| JP | 02-298239 | 12/1990 |
| JP | 03-203998 | 9/1991 |
| JP | 2010-505388 A | 2/2010 |
| KR | 10-2009-0029708 | 3/2009 |
| WO | 9837045 A1 | 8/1998 |
| WO | WO-98/37045 | 8/1998 |
| WO | WO-2009/140695 A2 | 11/2009 |

OTHER PUBLICATIONS

WIPO, "International Search Reprt and Written Opinion of the International Searching Authority", dated Sep. 22, 2014.
Database CA [Online] Chemical Abstracts Service, Columbus, Ohio, US; IL'IN, A. I. et al: "Alkaline purification of alcohols separated from unsaponifiables-II", STN Database accession No. 1969:12825.
Office Action issued on Chinese Application 201480022365.2, dated Aug. 31, 2016, English translation provided.
Examination Report issued on Australian Application 2014225436, dated Oct. 4, 2017.
Office Action issued on Japanese Application 2015-561715, dated Aug. 16, 2017, English translation only.
Examination Report issued on Australian Application 2014225436, dated May 2, 2017.
Maslozhirovaia promyshlennost, 1968, vol. 34, pp. 22-23 (English translation not available.
Notice of Reasons for Rejection issued on Japanese application 2015-561715, dated Sep. 26, 2016, English translation only.
Office Action issued on Chinese Application 201480022365.2, dated Jun. 21, 2017, English translation provided.
Decision of Rejection on JP Patent Application No. 2017-241266 dated Oct. 3, 2019 (with English translation) (4 pages).
Examination Report on European Patent Application No. 14717901. 4, dated Feb. 4, 2019 (4 pages).
Notice of Reasons for Rejection in JP Patent Application No. 2017-241266 dated Nov. 29, 2018 (with English translation) (8 pages).
Official Action on Colombian Patent Application No. 15-231.793 dated Jul. 16, 2018 (no English translation available) (12 pages).
Substantive Examination Report Stage I on ID Patent Application No. P00201506244 dated Jul. 11, 2019 (with English translation) (5 pages).
Second Office Action in MX Patent Application No. MX/a/2015/ 011738 dated Oct. 24, 2019 (with English translation).
Preliminary Office Action on BR Patent Application No. 112015021763.0 dated Oct. 16, 2019 (with English translation) (6 pages).
Substantive Examination Adverse Report in MY Patent Application No. PI2015002213 dated Oct. 30, 2019 (2 pages).

(Continued)

*Primary Examiner* — Ana Z Muresan
(74) *Attorney, Agent, or Firm* — Harness Dickey & Pierce P.L.C.

(57) ABSTRACT

The disclosure relates to downstream processing of fatty alcohol (FALC) and provides a novel purification method that provides FALC at high purity and yield.

16 Claims, No Drawings

(56) References Cited

OTHER PUBLICATIONS

Substantive Examination Report Stage II in ID Patent Application No. P00201506244 dated Feb. 5, 2020, 5 pages.
Third Office Action in MX Patent Application No. MX/a/2015/011738 dated Jul. 17, 2020 (no English translation available).
First Examination Report in in Patent Application No. 201918045614 dated Jun. 9, 2020 (5 pages).
Pre-Appeal Examination Report in JP Patent Application No. 2017-241266 dated May 26, 2020 (with English translation)(4 pages).
Notification of Reasons for Refusal in KR Patent Application No. 10-2015-7027462 dated Apr. 24, 2020 (with English translation) (14 pages).
Office Action in CA Patent Application No. 2904406 dated Mar. 12, 2020 (4 pages).
Extended European Search Report from corresponding European Application No. 20183045.2 dated Dec. 7, 2020.

DOWNSTREAM PROCESSING OF FATTY ALCOHOL COMPOSITIONS PRODUCED BY RECOMBINANT HOST CELLS

CROSS-REFERENCE TO RELATED APPLICATIONS

This application claims the benefit of U.S. Provisional Application No. 61/774,375, filed Mar. 7, 2013, the contents of which are hereby incorporated in their entirety.

FIELD

The disclosure relates to downstream processing of fatty alcohols. Herein, the disclosure encompasses a novel purification method that provides fatty alcohols at high purity and yield.

BACKGROUND

Fatty alcohols have many commercial uses. The shorter chain fatty alcohols are used in the cosmetic and food industries as emulsifiers, emollients, and thickeners. Due to their amphiphilic nature, fatty alcohols behave as nonionic surfactants, which are useful in personal care and household products, such as, for example, detergents and cleaning compositions. In addition, fatty alcohols are used in waxes, gums, resins, pharmaceutical salves and lotions, lubricating oil additives, textile antistatic and finishing agents, plasticizers, cosmetics, industrial solvents, and solvents for fats. Fatty alcohol (FALC) can be obtained from palm oil, palm kernel oil, vegetable oils, soybean or tallow, albeit at considerable financial and environmental costs. When FALC is derived from conventional sources (e.g., vegetable oil, palm oil, etc.), the initial mixture contains numerous impurities including free fatty acids, fatty acid methyl ester (FAME), heavy fatty-fatty esters (i.e., long chain molecules including C20 to C30) as well as other impurities.

FALC can also be obtained from the fermentation (culture) of a microorganism, which has been engineered to produce FALC having chain-length from C6 to C18. Under certain culture conditions, crude FALC that is produced from a microbial fermentation broth can contain, in addition to FALC, certain impurities. Such impurities include, but are not limited to, free fatty acids (FFA); fatty-fatty esters (FFE); fatty aldehydes, fatty ketones and carbonyl-containing compounds; sulfur and metallic compounds; water and additional impurities. Impurities are typically removed from FALC to meet final product specifications. Removal of FFA (de-acidification) is commonly carried out by alkaline refining methods (i.e., via chemical methods) and physical refining methods (i.e., via evaporation of FFA) such as in commercial operations. Conventional alkaline refining methods are not without shortcomings; particularly they are prone to experiencing difficulties when attempting to separate the finely dispersed and partially solubilized soap (e.g., C8-C18 chain-length) away from FALC, which happens during centrifugation followed by water-washing. Generally, alkaline refining methods are encumbered with unacceptably high alcohol loss and FFE contamination, which must be reduced via a separate processing step. In addition, physical refining is nearly impossible because FALC, FFA and FFE have similar boiling points. Moreover, FFA have a chain-length distribution similar to FALC and some of the FFE overlap in chain-length with FALC. Thus, on a commercial scale, alkaline- and physical refining methods are not suitable for removal of FFA and FFE that are present in crude FALC. Thus, newer and better methods are needed that produce FALC with characteristics (e.g., purity) required to meet the specifications required for the use in particular products.

SUMMARY

One aspect of the disclosure provides a method of purifying a fatty alcohol (FALC), including (a) providing a starting material including FALC and saponifiable impurities; (b) adding a strong base to the starting material to generate a first mixture; and (c) evaporating the first mixture to generate a second mixture enriched for FALC. In one embodiment, the saponifiable impurities include free fatty acid (FFA), fatty-fatty ester (FFE), and carbonyl-containing compounds. In another embodiment, the strong base comprises 0.3 to 0.6 weight percent excess sodium hydroxide (NaOH). In another embodiment, the strong base reduces the FFA and the FFE by neutralizing the FAA and saponifying the FEE, wherein saponifying the FEE generates additional FFA for neutralization and additional FALC. The strong base further reduces the carbonyl-containing compounds. In yet another embodiment, the neutralizing and saponifying is carried out at a temperature of about 100° C. to about 130° C., at ambient pressure to partial vacuum of about 80 torr. In still another embodiment, the neutralizing and saponifying is carried out for about 2 to 4 hours. In yet another embodiment, the amount of FFA in the second mixture is less than about 0.03 mg KOH/g sample and the amount of FFE in the second mixture is less than about 0.4 mg KOH/g sample. In another embodiment, the amount of sodium soap in the second mixture is less than about 20 ppm. The FALC obtained in the second mixture is usually about 98% pure.

Another aspect of the disclosure provides a method of purifying FALC, including (a) providing a starting material including FALC and saponifiable impurities; (b) adding a strong base to the starting material to generate a first mixture; (c) evaporating the first mixture to generate a second mixture enriched for FALC; and (d) bleaching the second mixture with a bleaching agent to generate bleached FALC. In one embodiment, the bleaching agent includes, but is not limited to, hypochlorite, a peroxide, a bleaching clay, and an absorbent. In another embodiment, the bleaching agent is effective to remove metallic compounds; color bodies; trace levels of additional impurities including oxidized fatty compounds or fatty compounds with free radicals, or combinations thereof.

Another aspect of the disclosure provides a method of purifying FALC, including (a) providing a starting material including FALC and saponifiable impurities; (b) adding a strong base to the starting material to generate a first mixture; (c) evaporating the first mixture to generate a second mixture enriched for FALC; (d) bleaching the second mixture with a bleaching agent to generate bleached FALC; and (e) hydrogenating the second mixture with hydrogen and a catalyst to generate hydrogenated FALC. In one embodiment, the hydrogenating includes, but is not limited to, a one pot slurry reaction, a slurry reaction followed by a packed bed reaction, and two packed bed reactions in series. In another embodiment, the method further includes fractionating the hydrogenated FALC according to boiling point, wherein FALC having a difference in chain length of two or more carbons are separated. In another embodiment, the hydrogenated FALC comprises at least about 50 percent $C_{12}$ to $C_{18}$ fatty alcohol.

Another aspect of the disclosure provides a method of purifying FALC, wherein the starting material comprises at least 0.1 to 0.5 weight percent of FFA and/or at least 0.1 to 05 weight percent of FFE. The starting material may further include at least 0.1 to 0.5 weight percent carbonyl-containing compounds. In addition, the starting material may further include less than 1 weight percent dialcohol compounds. The starting material may further include sulfur or at least one sulfur-containing compound and/or water. In one embodiment, the starting material is a product of a fermentation broth. In another embodiment, the fermentation broth is an *E. coli* fermentation broth. In yet another embodiment the starting material encompasses a saponification (SAP) value of about 20 mg KOH/g or less.

Another aspect of the disclosure provides a method of purifying FALC, including (a) providing a starting material including FALC and saponifiable impurities; (b) adding a strong base to the starting material to generate a first mixture; and (c) evaporating the first mixture to generate a second mixture enriched for FALC, wherein the evaporating is conducted at a temperature of less than about 150° C. at about 1 torr. In another embodiment, the evaporating is conducted at a temperature of less than about 187° C. at about 5 torr. In yet another embodiment, the evaporating is conducted at a temperature that corresponds to a vapor pressure of a $C_{18}$ alcohol.

DETAILED DESCRIPTION

The development of a new purification method provides a significantly higher fatty alcohol yield over known alkaline refining methods and is used to produce fatty alcohol with characteristics required to meet the specifications for particular products including higher purity. The new method involves neutralization and saponification of a starting material. As such, the new method includes adding a strong base to a starting material that includes fatty alcohol (FALC) and saponifiable impurities. Such impurities include, for example, free fatty acids (FFA), fatty-fatty esters (FFE), and carbonyl-containing compounds. The starting material is usually derived from a microorganism grown in a fermentation broth. When the strong base is added to the starting material it reduces the FFA and FFE by neutralizing the FFA and saponyfing the FFE in the mixture. In addition, the strong base oxidizes some carbonyl-containing compounds in the mixture into FFA, and reduces other carbonyl-containing compounds into aldehydes and ketones, which further split into FFA. The saponification of FFE results in the generation of additional FFA and FALC, wherein the FFA is again neutralized and thereby saponified. At some point, all FFA has have been converted to soap and FALC is enriched. Therefore, saponification of FFE and neutralization of FFA using an excess strong base converts nearly all the FFA and nearly all the FFE to soaps, resulting in a solution highly enriched for FALC. Using subsequent fatty alcohol evaporation produces a high purity FALC nearly free from FFA, FFE, and salts. Surprisingly, the Applicants have found that this simple two-step method results in about 98% pure FALC. Accordingly, the disclosure provides a new and better method of purifying FALC from a starting material comprising FALC and saponifiable impurities. The final mixture is enriched for FALC, wherein the amount of soap (i.e., the salt of FFA) in the final mixture is less than 20 ppm. The new method produces a FALC product that is nearly free from FFA and FFE, wherein FFA are about 0.1% (e.g., about 0.05%, about 0.03%, or about 0.01%), and wherein FFE have about a 0.5 saponification (SAP) value (e.g., about 0.4, about 0.3, or about 0.2).

The starting material can comprise any combination of FALC and saponifiable impurities, including, FFA, FFE, and/or carbonyl-containing compounds at a certain weight percent (wt %). In a preferred embodiment, the starting material comprises at least about 0.5 (wt %) (e.g., at least 1.0 wt %) FFE and/or at least about 0.5 wt % (e.g., at least 1.0 wt %) FFA and/or at least about 0.5 wt % (e.g., at least 1.0 wt %) carbonyl-containing compounds. The starting material typically will comprise less than about 5 wt % (e.g., less than 4 wt %, less than 3 wt %, less than 2 wt %, and/or less than 1 wt %) of carbonyl-containing compounds. The starting material can also include other components and/or impurities, such as less than about 1 wt % (e.g., less than 0.5 wt %) dialcohol compounds, sulfur, at least one sulfur-containing compound, and/or water at less than about 5 wt % (e.g., less than 3.5 wt %). Preferably, the starting material comprises a saponification (SAP) value of about 20 mg (e.g., 15 mg, 10 mg, 5 mg, or 2 mg) KOH/g or less. An example of a starting material comprises less than about 10 wt % FFA, less than about 5 wt % FFE, less than about 2 wt % carbonyl-containing compounds, about 250 ppm sulfur, about 3.5 wt % water, and a remaining portion containing fatty alcohols ranging from $C_6$ to $C_{18}$. In one embodiment of the disclosure, the starting material is a product of a fermentation broth. The fermentation broth can be, for example, a microbial fermentation broth, such as an *E. coli* fermentation broth. The microbial cell preferably is genetically engineered to optimize FALC production. Methods and compositions for optimizing FALC production in genetically engineered microbial cells are described, for example, in U.S. Patent Application Publications 2012/0142979, 2011/0256599, 2011/0250663, and 2010/0105963.

A strong base is any base that hydrolyzes (e.g., completely hydrolyzes) and can neutralize the FFA and saponify the FFE. Typically, such a strong base is a hydroxide of a Group I or II alkali metal. Strong bases include, for example, potassium hydroxide, barium hydroxide, cesium hydroxide, sodium hydroxide, strontium hydroxide, calcium hydroxide, lithium hydroxide, and rubidium hydroxide. In one preferred embodiment, the strong base is sodium hydroxide. The strong base can be used in any suitable concentration to neutralize the FFA and saponify the FFE. In general, an excess of a strong base will be used, such as about 0.01 wt % or more (e.g., 0.05 wt % or more, 0.1 wt % or more, 0.2 wt % or more, 0.3 wt % or more, 0.4 wt % or more, or 0.5 wt % or more excess base to total SAP value relative to the starting material). Alternatively (or in addition), the excess of the strong base used can be about 1.0 wt % or less, (e.g., 0.9 wt % or less, 0.8 wt % or less, 0.7 wt % or less, 0.6 wt % or less, 0.5 wt % or less, or 0.4 wt % or less excess base to total SAP value relative to the starting material). Thus, the excess of the strong base can be in an amount bound by any two of the above endpoints (e.g., 0.1-0.5 wt %, 0.3-0.6 wt %, 0.5-1.0 wt %, 0.6-0.8 wt %, or 0.05-1.0 wt %). For example, saponification of FFE into FFA and fatty alcohol and neutralization of overall FFA has been effectively achieved herein using excess 0.2-0.5 wt % NaOH. The theoretical amount of NaOH accounts for FFA, FFE, and carbonyl in the crude fatty alcohol. The strong base typically will be used in the form of an aqueous mixture comprising at least about 1 wt % (e.g., at least 5 wt %, at least 10 wt %, at least 15 wt %, at least 20 wt %, at least 25 wt %, at least 30 wt %, at least 40 wt %, at least 50 wt %, and at least 60 wt % of base). The soap (i.e., salt of FFA) is the by-product of the saponification reaction between the FFA and the strong base. The soap depends on the nature of the alkali used for the strong base and includes, for example, members of Group I (e.g., Li, Na, K, etc.) and/or Group II (e.g., Mg, Ca, etc.). In one preferred embodiment, the soap is a sodium soap.

Typical neutralization/saponification process conditions include an operating temperature in the range of 110° C.-140° C., a reaction time of at least 1 hour, and/or pressures ranging from ambient pressure to partial vacuum of 360 torr. In one embodiment of the disclosure, the generation of the first mixture (e.g., the FFA neutralization and FFE saponification) can be conducted, for example, at about 80° C.-180° C. for about 0.5-4 hours with an excess of about 0.05-1.0 wt % base to total SAP value relative to the starting material. As FFA is neutralized, the crude fatty alcohol's viscosity increases substantially. Typically, neutralized crude fatty alcohol can be solidified at temperatures below about 110° C. when moisture is completely removed. At a temperature greater than about 130° C., neutralized and de-moisturized crude fatty alcohol, having FFA levels up to about 10%, is observed to be in the liquid phase.

Typically, the starting material contains moisture (e.g., at least 1 wt %, at least 2 wt %, at least 3 wt %, at least 4 wt %, and at least 5 wt %; but less than 10 wt %, less than 8 wt %, and less than 6 wt %). For example, a starting material can comprise about 3.5 wt % water. Extra moisture, by the addition of 20%-50% base solution and moisture generation during FFA neutralization, causes significant foaming during fatty alcohol evaporation. A moisture drying process (e.g., with operating temperatures around 130° C. and 80 torr) can be installed either before or after the SAP reduction reaction, which typically is operated at 130° C. and 360 torr for 2 hours. Partial vacuum can be applied to reduce oxidation of fatty alcohol product in both drying and SAP reduction reaction steps. A small amount of hexanol presented in the crude fatty alcohol is an undesirable byproduct component, and it can be removed simultaneously during the moisture drying step to reach the level desired for subsequent downstream processing. The step of neutralizing the FFA and saponifying the FFE (i.e., hydrolyzing) with a strong base can include reducing the amount of carbonyl-containing compounds (e.g., fatty aldehydes and fatty ketones). For example, the concentration of carbonyl-containing compounds is reduced by at least 1%, at least 5%, at least 10%, at least 15%, at least 20%, at least 25%, at least 30%, at least 40%, at least 50%, at least 60%, at least 70%, at least 80%, or at least 90%. The evaporation can be conducted at a vapor temperature of about 155° C. at 1 torr, 187° C. at 5 torr, or at a temperature that corresponds to the vapor pressure of a $C_{18}$ alcohol. The vapor temperature typically is measured at the top of an entrainment separator. A VLE graph of normal paraffin alcohols can be used to determine the vapor temperature and vacuum level. When evaporation is complete, the highly viscous evaporator bottom contains fatty alcohol (mostly $C_{18}OH$), salts, and excess base. To maintain a liquid or gel state in the evaporator bottom, the temperature is typically kept around 130° C. or higher. The evaporator bottom temperature is typically 10-50° C. higher than the corresponding vapor temperature, which is determined by the pressure drop from the evaporation surface to the complete condensation point. The evaporator bottom temperature, therefore, depends on the equipment employed. The distillate of the crude FALC evaporation is termed "EC-FALC", wherein producing EC-FALC is optional (see Example 3). Total SAP of EC-FALC is about 6.5 mg KOH/g (2.5% FFA equivalent).

As noted above (supra), typical neutralization/saponification conditions include an operating temperature in the range of about 110° C.-140° C. (e.g., 100-130° C.), a reaction time of at least 1 hour (e.g., 2-4 hours), and/or pressures ranging from ambient pressure to partial vacuum of 360 torr (e.g., 80 torr). In a specific example, a neutralization and saponification process conducted at about 130° C. for about 2 hours employing 0.3-0.5 wt % excess NaOH produces sodium-salts and fatty alcohol with non-detectable level of FFA, less than 0.2 SAP value and significantly reduced carbonyl concentration In another specific example, a neutralization and saponification process conducted at about 130° C. for about 4 hours at about 80 torr employing about 0.4 wt % excess NaOH produces sodium-salts and fatty alcohol with similarly non-detectable level of FFA, less than 0.2 SAP value and significantly reduced carbonyl concentration. Evaporation of neutralized/saponified fatty alcohol is conducted at about 155° C. of vapor temperature at 1 torr, about 187° C. at 5 torr, or at a temperature that corresponds to the vapor pressure of a $C_{18}$ alcohol removes all sodium salts and reduces sulfur concentration in the distillate to 20-30 ppm. The yield of fatty alcohol distillate can be about 98% or greater of fatty alcohol content in the crude fatty alcohol that contains about 5% FFA and an overall SAP value OF greater than 20 mg KOH/g.

The method can further comprise (d) acidulating the distillation bottom of the first mixture (neutralized/saponified fatty alcohol) to generate an acidulated bottom. Any suitable acid can be used, such as a mineral acid or an organic acid (e.g., sulfonic acid, carboxylic acid). Examples of mineral acids include, but are not limited to, hydrochloric acid, hydrobromic acid, hydroiodic acid, hypochlorous acid, chlorous acid, chloric acid, perchloric acid, sulfuric acid, fluorosulfuric acid, nitric acid, phosphoric acid, hexafluorophosphoric acid, chromic acid, and boric acid. Examples of organic acids include, but are not limited to, methanesulfonic acid, p-toluenesulfonic acid, acetic acid, citric acid, lactic acid, gluconic acid, and formic acid. In one preferred embodiment, the acid is a mineral acid (e.g., sulfuric acid). The acid can be used in any suitable concentration to acidulate the first mixture (neutralized/saponified fatty alcohol). For example, the acid can be an aqueous mixture comprising at least about 1 wt % (e.g., at least 5 wt %, at least 10 wt %, at least 15 wt %, at least 20 wt %, and at least 25 wt %) of acid. An in-situ acidulation process can be carried out to simulate a commercial process, in which discharge of the bottoms from a wiped film evaporator below 240° C. can be acidulated via an intense in-line mixer or in a batch mixing tank. In a particular example, a 20% stoichiometric excess of 20 wt % sulfuric acid solution was used to react with sodium soap and residual NaOH to form FFA, $Na_2SO_4$, and water. This process was carried out by keeping the evaporator bottom temperature at 130° C. and under ambient pressure. The addition of 20 wt % sulfuric acid solution was slowly introduced to not cause excessive water vapor fumes. As the acid dosage increased, the evaporator bottom temperature decreased to about 100° C. The resulting evaporator bottom was completely liquefied after 10 minutes of reaction time at 100° C. At this stage, about an equal volume of deionized water was added to the completely liquefied evaporator bottom for cleaning purposes and to dilute the acidulated mixture. After the heat was turned off, the resulting mixture was mixed overnight to thoroughly clean the evaporation setup.

A starting material can comprise up to 40-90% monounsaturated fatty alcohol of various chain lengths. In certain embodiments, the FALC is at least 5, at least 6, at least 7, at least 8, at least 9, at least 10, at least 11, at least 12, at least 13, at least 14, at least 15, at least 16, at least 17, at least 18, or at least 19, carbons in length. Alternatively, or in addition, the FALC is 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the FALC can have a chain length bounded by any two of the above endpoints. For example, the R group can be 6-16 carbons in length, 10-14 carbons in length, or 12-18 carbons in length. In some embodiments, the FALC is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ FALC. In certain embodiments, the FALC is a $C_{12}$, $C_{13}$, $C_{14}$, $C_{15}$, $C_{16}$, $C_{17}$, or $C_{18}$ FALC. The starting material can comprise FALC of any of the foregoing chain lengths in any amounts. A starting material can also comprise branched or unbranched FALC. Branched chains may have more than one point of branching and may include cyclic branches. In some embodiments, the branched FALC is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ branched FALC. In one embodiment, the branched FALC is a $C_6$, $C_8$, $C_{10}$, $C_{12}$, $C_{13}$, $C_{14}$, $C_{15}$, $C_{16}$, $C_{17}$, or $C_{18}$ branched FALC. In another embodiment, the hydroxyl group of the branched FALC is in the primary ($C_1$) position. In another embodiment, the branched FALC is an iso-fatty alcohol, or an anteiso-fatty alcohol. In yet another embodiment, the branched FALC includes, but is not limited to, iso-$C_{7:0}$, iso $C_{8:0}$, iso $C_{9:0}$, iso-$C_{10:0}$, iso-$C_{11:0}$, iso-$C_{12:0}$, iso-$C_{13:0}$, iso-$C_{14:0}$, iso-$C_{15:0}$, iso-$C_{16:0}$, iso-$C_{17:0}$, iso-$C_{18:0}$, iso-$C_{19:0}$, anteiso-$C_{7:0}$, anteiso-$C_{8:0}$, anteiso-$C_{9:0}$, anteiso-$C_{10:0}$, anteiso-$C_{11:0}$, anteiso-$C_{12:0}$, anteiso-$C_{13:0}$, anteiso-$C_{14:0}$, anteiso-$C_{15:0}$, anteiso-$C_{16:0}$, anteiso-$C_{17:0}$, anteiso-$C_{18:0}$, and anteiso-$C_{19:0}$ branched fatty alcohol. Further, a starting material can comprise saturated or unsaturated FALC. If unsaturated, the FALC can have one or more than one point of unsaturation. In one embodiment, the unsaturated FALC is a monounsaturated FALC. In another embodiment, the unsaturated FALC includes, but is not limited to, a C6:1, C7:1, C8:1, C9:1, C10:1, C11:1, C12:1, C13:1, C14:1, C15:1, C16:1, C17:1, C18:1, C19:1, C20:1, C21:1, C22:1, C23:1, C24:1, C25:1, and a C26:1 unsaturated FALC. In certain embodiments, the unsaturated FALC is C10:1, C12:1, C14:1, C16:1, or C18:1. In other embodiments, the unsaturated FALC is unsaturated at the omega-7 position. In still other embodiments, the unsaturated FALC comprises a cis-double bond.

Unsaturated FALC can be converted to complete or near complete saturation. Accordingly, the method can further comprise (d) hydrogenating the second mixture with hydrogen and a catalyst to generate hydrogenated FALC. The hydrogenating step can be performed using methods known in the art, including a one pot slurry reaction, a slurry reaction followed by a packed bed reaction, two packed bed reactions in series, or a combination of these techniques. The hydrogenated FALC comprises at least about 50% (e.g., at least 55%, at least 60%, at least 65%, at least 70%, at least 75%, and at least 80%) $C_{12}$ to $C_{18}$ fatty alcohol. In general, the hydrogenated FALC will comprise up to about 100% (e.g., up to 99%, up to 97%, up to 95%, up to 93%, up to 91%, up to 88%, and up to 85%) $C_{12}$ to $C_{18}$ fatty alcohol. The hydrogenated FALC can comprise any range in any combination of the foregoing values, such as 50-99%, 55-97%, and the like, of $C_{12}$ to $C_{18}$ fatty alcohol. Key parameters that determine the hydrogenation reaction stoichiometry and kinetics are saturation level of the feed fatty alcohol (as measured by Iodine Value (IV)), fatty alcohol density, hydrogen solubility in the fatty alcohol, catalyst loading, and reaction temperature and/or pressure. In addition to performing IV titration, the saturation level can also be determined through GC or GC-MS analysis. A catalyst can be used to drive the hydrogenation reaction. In the first reaction step, thermally and/or kinetically unsaturated fatty alcohol starts to rotate under the reaction conditions to reform from the cis to the trans position. The trans fatty alcohols generally are favored for hydrogenation reactions due to their lower energy state. Hydrogen is then added across the double bond at the catalyst surface to form saturated fatty alcohols. Completeness of the hydrogenation reaction is dependent on the choice of catalyst, catalyst load, reaction conditions, and time. A number of catalysts can be used for the fatty alcohol hydrogenation process. Commercially available catalysts include zinc, nickel, palladium, platinum, and copper-chromium. Nickel-based catalysts are lower in cost, however the reaction kinetics can be slower, selectivity can be less and the catalyst can be more readily fouled. Nickel can be used as an initial reactor that provides a major reduction in unsaturation, as measured by IV titration. Palladium- and platinum-based catalysts are known to have better saturation reaction kinetics and better selectivity. The cost of these catalysts is substantially higher than nickel, and they can be best used in a polishing hydrogenation step in order to get full saturation (i.e., IV<0.1). A copper-chromium catalyst can also be used. In one specific example, nickel is used as a catalyst. Catalyst load and catalyst life span are highly dependent on saturation completeness, reaction kinetics and potential impurities in the feed stream. Typical amounts of catalyst are at least about 0.01 wt % (e.g., at least 0.02 wt %, at least 0.03 wt %, at least 0.05 wt %, at least 0.08 wt %, at least 0.1 wt %, at least 0.2 wt %, at least 0.5 wt %, at least 1 wt %, and at least 1.5 wt %). Usually the amount of catalyst is less than about 10 wt % (e.g., less than 8 wt %, less than 5 wt %, less than 3 wt %, less than 2 wt %, less than 1 wt %, less than 0.5 wt %, less than 0.1 wt %, less than 0.08 wt %, and less than 0.05 wt %). The amount of catalyst can also comprise any range in any combination of the foregoing values, such as 0.01-10 wt %. Generally, catalysts can be a major contributor in the hydrogenation process cost. As a result, measures should be taken to remove impurities in the fatty alcohol feed that could potentially inactivate the catalyst and shorten its useful life cycle. Impurities such as sulfur, phosphorus, selenium, sodium, magnesium, potassium, calcium, silica, and nitrogen compounds (e.g., amino acid, peptides, proteins, and amines) are known to have some detrimental impact on catalysts. Evaporation can significantly reduce these impurities, as well as removing antifoam (if any present), color bodies and free fatty acids (FFA).

In any of the foregoing methods, the hydrogenating step is a one pot slurry reaction, and the hydrogenating step is conducted with 1-3 wt % nickel catalyst at 100-135° C. at 100-500 psi for about 4-8 hours, resulting in a FALC product that is at least about 97% (e.g., at least 98% or at least 99%) pure with a yield of total FALC product of at least about 90%, wherein the FALC product has an Iodine Value ("IV") of less than about 0.3 and a carbonyl level of less than about 150 ppm. Alternatively, the hydrogenating step is a slurry reaction followed by a packed bed reaction, wherein the slurry reaction is conducted with 0.03-0.05 wt % nickel catalyst at about 100-135° C. and about 100-500 psi for about 0.5-2 hours, and the packed bed reaction is carried out for 4-8 hours residence time equivalent using a pelletized nickel catalyst at 100-135° C. and about 100-500 psi resulting in a FALC product that is at least about 97% (e.g., at least 98% or at least 99%) pure with a yield of total FALC product of at least about 90%, wherein the FALC product has an Iodine Value ("IV") of less than about 0.3 and a carbonyl level of less than about 150 ppm. In addition, the hydrogenating step can be two packed bed reactions in series with 0.5-1 hour equivalent nickel residence time for a first packed bed reactor followed by 4-8 hours residence time equivalent using a pelletized nickel catalyst at 100-135° C. and about 100-500 psi resulting in a FALC product that is at least about 97% (e.g., at least 98% or at least 99%) pure with a yield of total FALC product of at least about 90%, wherein the FALC product has an Iodine Value ("IV") of less than about 0.3 and a carbonyl level of less than about 150 ppm. Prior to the hydrogenation in step (d), the method can further comprise bleaching of the second mixture (e.g., distillate of neutralized/saponified FALC) with a bleaching agent. The bleaching agent is any suitable material, such as a hypochlorite, a peroxide, a bleaching clay, an absorbent material effective to remove metallic compounds (e.g., sulfur, phosphorus, sodium, calcium, magnesium, etc.), color bodies, and/or trace levels of other impurities. The bleaching agent can also comprise a combination of any of the foregoing materials. In one embodiment of the disclosure, a bleaching clay, such as F-160 (BASF) or Biosil (Süd Chemie), is used. The spent bleaching clay can be removed through MF (micro-filter) filtration. Any suitable amount of bleaching agent can be used so long as the amount is effective in removing impurities, such as metallic compounds and color bodies. Typical amounts include at least 0.1 wt %, at least 0.2 wt %, at least 0.3 wt %, at least 0.4 wt %, at least 0.5 wt %, at least 0.6 wt %, at least 0.8 wt %, at least 1 wt %, and at least 2 wt %. Examples of the conditions used for the bleaching step are described herein, but typically the temperature will range from about 80-120° C. (e.g., 105-115° C.) and/or about 60-100 torr (e.g., 60 torr, 70 torr, 80 torr, 90 torr, or 100 torr). The time period for bleaching will depend on the concentration of components in the starting material, and the type and amount of bleaching agent. An example of a time period for bleaching is at least about 15 min (e.g., at least 20 min, at least 30 min, at least 45 min, at least 60 min, at least 90 min, and at least 120 min). The method can further comprise (e) fractionating the hydrogenated FALC under conditions in which FALC having a difference in chain length of two or more carbons are separated. In one exemplary process, a starting material comprising crude FALC undergoes the following process steps, as described herein: (A) FALC evaporation, (B) a consecutive saponification and evaporation, (C) bleaching, (D) one-pot hydrogenation, and (E) at least two-stage fractional distillation.

EXAMPLES

The following examples further illustrate the disclosure but, of course, should not be construed as in any way limiting its scope. Table 1 below describes some terms used herein.

TABLE 1

| FALC | DESCRIPTION |
|---|---|
| EC-FALC | Initially Evaporated FALC |
| SE-FALC | Saponified FALC |
| F-FALC | Bleached and Filtered SE-FALC |
| HF-FALC | Hydrogenated and Filtered BF-FALC |
| HFE-FALC | Distillate of HF-FALC |

Example 1

This example demonstrates the purification of crude FALC using neutralization & saponification followed by fatty alcohol evaporation.

The starting material comprised, inter alia, 88.6% crude FALC, 12.8 mg KOH/g sample of FFA, 7.3 mg KOH/g sample FFE, 1800 ppm carbonyl-containing compounds, and 3% moisture. A total of 2.23 wt % NaOH (with an excess of 0.61 wt % NaOH) was added to the starting material at 110° C. and 480 mbar and stirred for 2 hours. The mixture was then evaporated at 240° C. of bottom temperature and 2-4 torr to generate SE-FALC enriched for FALC. The composition of the mixture is set forth in Table 2.

The SE-FALC (distillate of neutralized/saponified FALC) includes an intermediate FALC where FFA and FFE impurities (meeting detergent or chemical feed stock specifications) can be removed through the saponification/evaporation (SAP/EVAP) process. Other impurities (carbonyl, sulfur and unsaturation) can be reduced through subsequent process steps, for example, bleaching, hydrogenation and fractional distillation.

TABLE 2

| Characteristic | Units | Crude Fatty Alcohol | SE-FALC |
|---|---|---|---|
| FALC | % | 88.6 | 99.7 |
| C6OH | % | 1.1 | 0.96 |
| Acid Number | mg KOH/g sample | 12.8 | Non-detectable |
| SAP (FFE) | mg KOH/g sample | 7.3 | 0.18 |
| Carbonyl | ppm | 1800 | 620 |
| Sulfur | ppm | 250 | <20 |
| Moisture | % | 3 | 0.1 |
| Sodium | ppm | <2 | <1 |
| Yield | % | — | 98.3 |

Example 2

This example demonstrates the results of three hydrogenation runs of a starting material comprising the BF-FALC (bleached and filtered SE-FALC) and a nickel catalyst. The feed represents the starting material before hydrogenation. Three different temperatures were run at 100 psig pressure using 0.27 grams of Pricat 9910, a nickel-based catalyst. The results are set forth in Table 3.

TABLE 3

| | Temperature (° C.) | FALC (g) | Unsaturated (GC %) | $H_2$ Added (g) | Iodine Value | Hydroxyl Value (HV) | Moisture (ppm) |
|---|---|---|---|---|---|---|---|
| Feed | — | — | 13.98 | — | 22 | 304 | 580 initial |
| | | | | | | | 2412 Run 3 |
| Run 1 | 125 | 211 | 0.19 | 0.297 | 1.8 | 302 | 1596 |
| Run 2 | 150 | 210 | 0 | 0.311 | 0.9 | 310 | 2206 |
| Run 3 | 170 | 211 | N/A | 0.305 | N/A | 313 | 2280 |

Both the IV and GC data in Runs 1 and 2 show significant redcution in unsaturation. Although Run 3 data is not available, the hydrogen consumption suggests that the degree of conversion is comparable. The hydroxyl value (HV) is an index of the number of intact hydroxyl group. A reduction in HV number would indicate a side reaction of those group to alkanes. Since there was no reduction in the HV, an operating temperature of 170° C. was feasible.

Example 3

This example demonstrates the purification of crude FALC in one embodiment of the disclosure. Several crude FALC samples having 1-2% FFA from pilot (1 m$^3$) or Fermic (20 m$^3$) fermentations were provided. An initial FALC evaporation step was employed to substantially reduce the FFA and FFE contents of the crude FALC to provide "EC-FALC." To recover near 100% of FALC with maximum reduction of FFA and FFE, the vapor temperature of evaporation was 187° C. at 5 torr or 155° C. at 1 torr, as measured at the top of the entrainment separator. Characteristics of the EC-FALC are provided in Table 4. The additional evaporation step to generate EC-FALC is optional and is only needed if the starting material contains high levels of FFA and FFE because such high levels of FFA and FFE can cause processing difficulties during the saponification/evaporation (SAP/EVAP) procedure.

nyl-containing compounds were oxidized to generate FFA, saponifiable compounds and long-chain compounds that have a higher boiling point than the saturated and unsaturated $C_{18}OH$. All of the FFA in the saponification reactor converted to sodium soap. Saponification was carried out at 110-130° C. and 60 torr for 2 hours. Subsequently, moisture was removed by lowering the vacuum to 20-30 torr for 1 hour. At the end of drying, the expected moisture content of the saponified EC-FALC is below 1000 ppm. The condensed water contained a significant amount of hexanol ($C_6OH$), but under these conditions, $C_6OH$ was only partially removed from the saponified EC-FALC. The dried saponified-EC-FALC was evaporated at 155° C. at 1 torr or 187° C. at 5 torr. The distillate of the first mixture (neutralized/saponified FALC) evaporation was termed as "SE-FALC." (e.g., second mixture FALC). An evaporator bottom temperature of 215° C. at 5 torr can provide a desirable yield. The soap phase in the evaporator can also be reasonably dry.

The soap value of the SE-FALC should be less than 30 ppm (0.01 acid # equivalent) when a proper entrainment or distillation column is equipped on the top of the evaporator. In order to achieve a continuous removal of soap and a maximum yield of FALC, a two-stage evaporation can be used for a commercial system. The two-stage commercial evaporation unit would consist of a falling-film, rising film or forced-circulation evaporator with packed column on the top of the evaporator followed by wiped-film evaporator

TABLE 4

| | unit | Crude FALC | EC-FALC | Mid-cut Specification | Comments |
|---|---|---|---|---|---|
| FALC purity | % | 87.9-94 | 96.5 | >98.9 | Dry basis |
| FALC comp. | | | | | FALC basis |
| $C_6OH:0$ | % | 1 | 1 | 0 | |
| $C_8OH:0$ | % | 3.2 | 3.2 | 0.3 | |
| $C_{10}OH:0$ | % | 4.1 | 4.1 | 1.0 | |
| $C_{12}OH$ (0, 1) | % | 59.9 | 59.9 | >65 | |
| $C_{14}OH$ (0, 1) | % | 21.2 | 21.5 | 21-28 | |
| $C_{16}OH$ (0, 1) | % | 8.3 | 8.3 | 4-8 | |
| $C_{18}OH$ (0, 1) | % | 2.2 | 2.2 | 0.5 | |
| $C_{12}OH + C_{14}OH$ | % | 81.1 | 90 | 86-93 | |
| $C_{12}OH/C_{14}OH$ | | 2.8 | 2.8 | 2.5-3.1 | |
| Average FALC MW | g/mole | 190 | 190 | 165 | |
| Moisture | ppm | 35,000 | <800 | 1000 | |
| Acid# | mg KOH/g | 6.7 | 1.5 | 0.1 | |
| SAP | mg KOH/g | 18.5 | 6.5 | 0.5 | |
| Carbonyls | ppm | 3472 | <1300 | 150 | FALD & ketones |
| Antifoam | ppm | 1000 | 125-250 | 130 | Dimethyl polysiloxane |
| Metals | | | | | |
| Si | ppm | 370 | 50-100 | ~53 | Mostly from antifoam |
| S | ppm | 200 | 7-20 | <1 | Mostly organic sulfur |
| Na | ppm | N/A | <1 | N/A | From saponification |
| Iodine Value (IV) | | 63 | 63 | <0.3 | (10): target IV |
| Hydrocarbon | % | ND | ND | <1 | |
| APHA color | | Dark brown | 20 | 10 | |

The EC-FALC had a total SAP of about 6.5 (~2.5% FFA equivalent).

Next, the EC-FALC was subjected to consecutive saponification/evaporation process (CSEP), which includes saponification, moisture drying, $C_6OH$ removal, and evaporation of saponified FALC to form "SE-FALC." (e.g., second mixture of FALC). A 0.2% wt-0.4% wt excess NaOH to total SAP value using 50% NaOH solution was added to EC-FALC to completely neutralize and to saponify the FFE. The saponified FFE was split into FFA and FALC. Some carbo- (WFE) with an entrainment separator on top of the WFE. In this example, a batch evaporator was employed to generate the SE-FALC. The evaporator has an effective heating capability from the side and bottom of reactor jackets and is equipped with a mixer with multiple blades to break-up a stable foam formed by soap and an entrainment separator at the top of the evaporator. An entrainment separator is also jacketed for either hot oil or steam heating to 190° C.

The characteristics of SE-FALC are provided in Table 5 below.

TABLE 5

| | unit | EC-FALC | SE-FALC | Mid-cut Specification | Comments |
|---|---|---|---|---|---|
| FALC purity | % | 96.5 | 99.0 | >98.9 | Dry basis |
| FALC comp. | | | | | FALC basis |
| $C_6OH:0$ | % | 1 | 0.5 | 0 | |
| $C_8OH:0$ | % | 3.2 | 3.2 | 0.3 | |
| $C_{10}OH:0$ | % | 4.1 | 4.1 | 1.0 | |
| $C_{12}OH$ (0, 1) | % | 59.9 | 59.9 | >65 | |
| $C_{14}OH$ (0, 1) | % | 21.5 | 21.5 | 21-28 | |
| $C_{16}OH$ (0, 1) | % | 8.3 | 8.33 | 4-8 | |
| $C_{18}OH$ (0, 1) | % | 2.2 | 2.2 | 0.5 | |
| $C_{12}OH + C_{14}OH$ | % | 81.4 | 81.4 | 86-93 | |
| $C_{12}OH/C_{14}OH$ | | 2.8 | 2.8 | 2.5-3.1 | |
| Ave. MW | g/mole | 190 | 190 | 165 | |
| Moisture | ppm | <800 | <500 | 1000 | |
| Acid# | mg KOH/g | 1.5 | ND | 0.1 | |
| SAP | mg KOH/g | 6.5 | <0.4 | 0.5 | |
| Carbonyls | ppm | <1300 | <900 | 150 | FALD & ketones |
| Antifoam | ppm | 125-250 | 125-250 | 130 | Dimethyl polysiloxane |
| Metals | | | | | |
| Si | ppm | 50-100 | 50-100 | ~53 | Mostly from antifoam |
| S | ppm | 7-20 | 7-15 | <1 | Mostly organic sulfur |
| Na | ppm | <1 | <1 | N/A | From saponification |
| Iodine Value (IV) | | 63 | 63 | <0.3 | 10 IV target |
| Hydrocarbon | % | ND | ND | <1 | |
| APHA color | | 20 | 5 | 10 | |

After completion of the saponification/evaporation process step, the SE-FALC has no detectable acid, <0.4 of SAP value, <1 ppm of Na, 50-100 ppm of Si, 7-20 ppm of sulfur, a faint yellow to very clear color, and IV about the same as the crude FALC. It also removed antifoam and the majority of color bodies from the EC-FALC. Partial reduction of carbonyl was also been observed through the saponification/evaporation step.

After completing the evaporation of neutralized/saponified EC-FALC, the soap generated remained in the evaporator bottom for the batch evaporation process. The soap phase contained about equal amount of soap and FALC. Acidulation of the soap in the evaporator was carried out to recover fatty species and CIP (clean-in-place) of the evaporator using $H_2SO_4$ at 100-130° C. for 1 hour. A 20% excess of $H_2SO_4$ (10% solution) was used. Complete CIP was achieved through one additional hour of cooking with an additional equal amount of DI water. The water addition was made to completely wet the reaction vessel surface coated with soap.

A bleaching unit operation was employed to protect the hydrogenation catalyst. Bleaching can reduce substantial amounts of sulfur, metallic impurities, color bodies, and other minute impurities from the SE-FALC. Bleaching was carried out at 115° C. and 80 torr with 0.5% of bleaching clay (F160 from BASF) for 1 hour of adsorption time. Then the mixture was cooled down to 60° C. before filtering. The bleached and filtered SE-FALC is referred to as "BE-FALC." Typically sulfur and sodium levels after bleaching are <5 ppm and <1 ppm, respectively. Faint yellow color can be minutely intensified due to oxidation under reaction temperature employed at partial vacuum. The characteristics of BE-FALC are provided in Table 6 below.

TABLE 6

| | unit | SE-FALC | BF-FALC | Mid-cut Specification | Comments |
|---|---|---|---|---|---|
| FALC purity | % | 99.0 | 99.0 | >98.9 | Dry basis |
| FALC comp. | | | | | FALC basis |
| $C_6OH:0$ | % | 0.5 | 0 | 0 | |
| $C_8OH:0$ | % | 3.2 | 3.2 | 0.3 | |
| $C_{10}OH:0$ | % | 4.1 | 4.1 | 1.0 | |
| $C_{12}OH$ (0, 1) | % | 59.9 | 59.9 | >65 | |
| $C_{14}OH$ (0, 1) | % | 21.5 | 21.5 | 21-28 | |
| $C_{16}OH$ (0, 1) | % | 8.3 | 8.3 | 4-8 | |
| $C_{18}OH$ (0, 1) | % | 2.2 | 2.2 | 0.5 | |
| $C_{12}OH + C_{14}OH$ | | 81.4 | 81.4 | 86-93 | |
| $C_{12}OH/C_{14}OH$ | | 2.8 | 2.8 | 2.5-3.1 | |
| Ave. MW | g/mole | 190 | 190 | 165 | |
| Moisture | ppm | <500 | <5000 | 1000 | |
| FFA (acid#) | mg KOH/g | ND | ~ND | 0.1 | |
| FFE (SAP) | mg KOH/g | <0.4 | <0.4 | 0.5 | |
| Carbonyls | ppm | <900 | <900 | 150 | FALD & ketones |
| Antifoam | ppm | 125-250 | <125 | 130 | Dimethyl polysiloxane |

TABLE 6-continued

|  | unit | SE-FALC | BF-FALC | Mid-cut Specification | Comments |
|---|---|---|---|---|---|
| Metals | | | | | |
| Si | ppm | 50-100 | <50 | ~53 | Mostly from antifoam |
| S | ppm | 7-15 | <5 | <1 | Mostly organic sulfur |
| Na | ppm | <1 | <1 | N/A | From saponification |
| Iodine Value (IV) | | 63 | 40 | <0.3 | 10 IV target |
| Hydrocarbon | % | ND | ND | <1 | |
| APHA color | | 5 | 20 | 10 | |

As seen in Table 6, carbonyl-containing compounds are the remaining impurity of BF-FALC. The level of unsaturated compounds was the same as the initial crude FALC (expressed as IV). Ideally, through hydrogenation, carbonyl-containing compounds and IV are reduced below 150 ppm and 0.15, respectively. PRICAT™ 9910 (Johnson Matthey, Billingham, England), a 22% active nickel catalyst on silica support that is coated with a fully saturated $C_{16}OH/C_{18}OH$ coating or a fully hardened vegetable oil (TAG) coating as a protective medium, can be used as a catalyst for a batch slurry hydrogenation. Pelletized nickel supported on silica or alumina can be used as a catalyst for the packed-bed hydrogenation. A two-stage hydrogenation (i.e., a batch slurry IV hydrogenation followed by packed-bed carbonyl hydrogenation and IV polishing) can be used. One-pot hydrogenation process conditions can be applied to cover both IV and carbonyl hydrogenation.

One-pot hydrogenation conditions typically can be 5-13% PRICAT™ 9910 catalyst (1.1-2.86% active Ni), 100-130° C., 100-300 psi (e.g., 250 psi) $H_2$, and 4-8 hours reaction time. $N_2$ is used to flush the reactor. After completion of hydrogenation, the hydrogenated FALC is cooled down to 60° C. for catalyst filtration. The sparkler (1 μm MF filter) filtration can be used for filtration of PRICAT™ 9910 catalyst. When TAG coated Pricat 9910 is used, the TAG (protective vegetable oil coating on the catalyst) will remain in the filtrate of the fully hydrogenated FALC. The fully hydrogenated/filtered FALC is called "HF-FALC". The TAG can be removed prior to fractional distillation by employing an evaporation step or removed as a final distillation bottom. The distillate of HF-FALC is termed as "HFE-FALC." The HFE-FALC must have IV<0.15, carbonyl<150 ppm, and negligible alkane. The characteristics of the HF-FALC and HFE-FALC are provided in Table 7 below.

TABLE 7

|  | unit | BF-FALC | HF-FALC | HFE-FALC | Midcut Final Product Specification | Comments |
|---|---|---|---|---|---|---|
| FALC purity | % | 99 | 99.2 | 99.7 | >98.9 | Dry basis |
| FALC comp. | | | | | | FALC basis |
| $C_6OH:0$ | % | 0 | 0 | 0 | 0 | |
| $C_8OH:0$ | % | 3.2 | 3.2 | 3.2 | 0.3 | |
| $C_{10}OH:0$ | % | 4.1 | 4.1 | 4.1 | 1.0 | |
| $C_{12}OH$ (0, 1) | % | 59.9 | 59.9 | 59.9 | >65 | |
| $C_{14}OH$ (0, 1) | % | 21.5 | 21.5 | 21.5 | 21-28 | |
| $C_{16}OH$ (0, 1) | % | 8.3 | 8.3 | 8.3 | 4-8 | |
| $C_{18}OH$ (0, 1) | % | 2.2 | 2.2 | 2.2 | 0.5 | |
| $C_{12}OH + C_{14}OH$ | | 81.4 | 81.4 | 81.4 | 86-93 | |
| $C_{12}OH/C_{14}OH$ | | 2.8 | 2.8 | 2.8 | 2.5-3.1 | |
| Average MW | g/mole | 190 | 190 | 190 | 165 | |
| Moisture | ppm | <500 | <500 | <500 | 1000 | |
| Acid# | mg KOH/g | ND | ND | ND | 0.1 | |
| SAP | mg KOH/g | <0.4 | <0.4 | <0.4 | 0.5 | |
| Carbonyls | ppm | <900 | 60 | 60 | <150 | FALD & ketones |
| Antifoam | ppm | <125 | | | | Dimethyl polysiloxane |
| Metals | | | | | | |
| Si | ppm | <50 | <50 | <50 | ~53 | Mostly from antifoam |
| S | ppm | <5 | <1 | <1 | <1 | Mostly organic sulfur |
| Na | ppm | <1 | <1 | <1 | N/A | From saponification |

TABLE 7-continued

| | unit | BF-FALC | HF-FALC | HFE-FALC | Midcut Final Product Specification | Comments |
|---|---|---|---|---|---|---|
| Iodine Value (IV) | | 63 | 0.05 | 0.05 | 0.3 | 10 IV target |
| Hydrocarbon | % | ND | negligible | negligible | <1 | |
| APHA color | | 20 | 5 | 5 | 10 | |

Table 8 presents the characteristics of a $C_8OH$-cut.

TABLE 8

| | unit | Light-cut Characteristics | $C_8OH$-cut Characteristics |
|---|---|---|---|
| FALC purity | % | >99.0 | >99.0 |
| FALC composition | | | |
| $C_6OH$:0 | % | 0 | 0 |
| $C_8OH$:0 | % | 43.4 | 98.0 |
| $C_{10}OH$:0 | % | 55.6 | 2.0 |
| $C_{12}OH$ (0, 1) | % | 1.0 | 0 |
| $C_{14}OH$ (0, 1) | % | 0 | 0 |
| $C_{16}OH$ (0, 1) | % | 0 | 0 |
| $C_{18}OH$ (0, 1) | % | 0 | 0 |
| $C_{12}OH + C_{14}OH$ | | — | — |
| $C_{12}OH/C_{14}OH$ | | — | — |
| Average MW | g/mole | 146 | 130 |
| Moisture | ppm | <500 | <500 |
| Acid# | mg KOH/g | ND | ND |
| SAP | mg KOH/g | <0.4 | <0.4 |
| Carbonyls | ppm | ~60 | ~60 |
| Antifoam | ppm | | |
| Metals | | | |
| Si | ppm | 50-100 | 50-100 |
| S | ppm | <1 | <1 |
| Na | ppm | <1 | <1 |
| Iodine Value (IV) | | 0.05 | 0.05 |
| Hydrocarbon | % | <1 | <1 |
| APHA color | | 5 | 5 |

Table 9 presents the characteristics of a $C_{10}OH$-cut.

TABLE 9

| | unit | Light-cut Characteristics | $C_{10}OH$-cut Characteristics |
|---|---|---|---|
| FALC purity | % | >99.0 | >99.0 |
| FALC comp. | | | |
| $C_6OH$:0 | % | 0 | 0 |
| $C_8OH$:0 | % | 43.4 | 1.0 |
| $C_{10}OH$:0 | % | 55.6 | 98.0 |
| $C_{12}OH$ (0, 1) | % | 1.0 | 1.0 |
| $C_{14}OH$ (0, 1) | % | 0 | 0 |
| $C_{16}OH$ (0, 1) | % | 0 | 0 |
| $C_{18}OH$ (0, 1) | % | 0 | 0 |
| $C_{12}OH + C_{14}OH$ | | — | — |
| $C_{12}OH/C_{14}OH$ | | — | — |
| Average MW | g/mole | ~146 | ~158.3 |
| Moisture | ppm | <500 | <500 |
| Acid# | mg KOH/g | ND | ND |
| SAP | mg KOH/g | <0.4 | <0.4 |
| Carbonyls | ppm | ~60 | ~60 |
| Antifoam | ppm | | |
| Metals | | | |
| Si | ppm | 50-100 | <50 |
| S | ppm | <1 | <1 |
| Na | ppm | <1 | <1 |
| Iodine Value (IV) | | 0.05 | 0.05 |
| Hydrocarbon | % | <1 | <1 |
| APHA color | | 5 | 5 |

Table 10 presents the characteristics of mid-cut FALC.

TABLE 10

| | unit | Light-cut bottom | Mid-cut characteristics | Mid-cut specification |
|---|---|---|---|---|
| FALC purity | % | 99.7 | 98.99 | >98.9 |
| FALC comp. | | | | |
| $C_6OH$:0 | % | 0 | 0 | |
| $C_8OH$:0 | % | 0 | 0 | 0.3 |
| $C_{10}OH$:0 | % | 1.0 | 1.1 | 1.0 |
| $C_{12}OH$ (0, 1) | % | 64.1 | 71.7 | >65 |
| $C_{14}OH$ (0, 1) | % | 23.0 | 25.7 | 21-28 |
| $C_{16}OH$ (0, 1) | % | 8.9 | 1.5 | 4-6 |
| $C_{18}OH$ (0, 1) | % | 2.4 | 0 | 0.5 |
| $C_{12}OH + C_{14}OH$ | | 87.9 | 97.4 | >96 |
| $C_{12}OH/C_{14}OH$ | | 2.8 | 2.8 | 2.5-3.1 |
| Average MW | g/mole | ~200 | 165 | 165 |
| Moisture | ppm | <500 | <500 | 1000 |
| Acid# | mg KOH/g | ND | ND | 0.1 |
| SAP | mg KOH/g | <0.4 | <0.4 | <0.4 |
| Carbonyls | ppm | 60 | 60 | <150 |
| Antifoam | ppm | | | |
| Metals | | | | |
| Si | ppm | <50 | <50 | ~53 |
| S | ppm | <1 | <1 | N/A |
| Na | ppm | <1 | <1 | <1 |
| Iodine Value (IV) | | 0.05 | 0.05 | <0.3 |
| Hydrocarbon | % | negligible | ND | <1 |
| APHA color | | 5 | 5 | 10 |

Table 11 presents the characteristics of heavy-cut FALC.

TABLE 11

| | unit | Light-cut bottom | Heavy-cut Characteristics |
|---|---|---|---|
| FALC purity | % | 99.7 | >99 |
| FALC comp. | | | |
| $C_6OH$:0 | % | 0 | 0 |
| $C_8OH$:0 | % | 0 | 0 |
| $C_{10}OH$:0 | % | 1.0 | 0 |
| $C_{12}OH$ (0, 1) | % | 64.1 | 0 |
| $C_{14}OH$ (0, 1) | % | 23.0 | 1 |
| $C_{16}OH$ (0, 1) | % | 8.9 | 78.5 |
| $C_{18}OH$ (0, 1) | % | 2.4 | 20.5 |

TABLE 11-continued

|  | unit | Light-cut bottom | Heavy-cut Characteristics |
|---|---|---|---|
| $C_{12}OH + C_{14}OH$ |  | 87.9 | — |
| $C_{12}OH/C_{14}OH$ |  | 2.8 | — |
| Average MW | g/mole | ~200 | ~248 |
| Moisture | ppm | <500 | <500 |
| Acid# | mg KOH/g | ND | ND |
| SAP | mg KOH/g | <0.4 | <0.4 |
| Carbonyls | ppm | 60 | ~60 |
| Antifoam | ppm |  |  |
| Metals |  |  |  |
| Si | ppm | <50 | <50 |
| S | ppm | <1 | <1 |
| Na | ppm | <1 | <1 |
| Iodine Value (IV) |  | 0.05 | 0.05 |
| Hydrocarbon | % | negligible | negligible |
| APHA color |  | 5 | 5 |

Table 12 summarizes the process conditions as described in this example.

TABLE 12

|  | Temp. °C. | Pressure psi | Reaction Time min | Vacuum torr | Reflux ratio | catalyst % |
|---|---|---|---|---|---|---|
| FALC Evap. | 187 | — | — | 5 |  |  |
| SAP reaction | 130 | — | 120 | 60 |  | — |
| SAP drying | 130 | — | — | 20-30 |  | — |
| SAP evap. | 187 | — | — | 5 |  | — |
| Bleaching | 115 | — | 60 | 80 |  | 0.5% F160 |
| Bleaching filtration | 60 | 30 | — | — |  | — |
| Hydrogenation | 100-130 | 250 | 240-480 | — |  | 5%-13% PRICAT ™ 9910 |
| Hydrogenation filtration | 60 | 30 | — | — |  | — |
| $C_8OH$-cut | tbd | — | — | tbd | tbd | — |
| $C_{10}OH$-cut | tbd | — | — | tbd | tbd | — |
| Mid-cut | tbd | — | — | tbd | tbd | — |
| Heavy-cut | tbd | — | — | tbd | tbd | — |

Fractional distillation conditions usually depend on the type of distillation equipment and one of skill can employ them as needed. The performance of each processing step is monitored to assure the quality of intermediates and final FALC products. The analytical requirement of crude FALC, intermediates, and final products are summarized in Table 13 below.

TABLE 13

|  | Acid# mg KOH/g | Total SAP mg KOH/g | Carbonyl ppm | IV | Soap ppm | S ppm | Na ppm | Si ppm | GC profile | Moisture ppm |
|---|---|---|---|---|---|---|---|---|---|---|
| Crude FALC | x | x | x | x |  | x | x | x | x | x |
| EC-FALC | x | x | x |  |  | x | x | x | x | x |
| SE-FALC | x | x | x |  | x | x | x | x | x | x |
| BE-FALC | x | x | x |  | x | x | x | x | x | x |
| HF-FALC | x | x | x | x | x | x | x | x | x | x |
| HFE-FALC | x | x | x | x | x | x | x | x | x | x |
| $C_8OH$-cut | x | x | x | x |  |  |  |  | x | x |
| $C_{10}OH$-cut | x | x | x | x |  |  |  |  | x | x |
| Mid-cut | x | x | x | x |  | x | x | x | x | x |
| Heavy-cut | x | x | x | x |  |  |  |  | x | x |

Example 4

This example demonstrates the purification of FALC in yet another embodiment of the disclosure. In this example, purification of FALC was carried out without employing the additional evaporation step to generate a form of crude FALC (i.e., EC-FALC; see Example 3). In addition, this example shows the high purity that can be achieved when FALC is enriched by the present method via neutralizing and saponyfing with a strong base to generate the first mixture, and then evaporating to generate the second mixture.

The starting material included about 89.95% even-chain FALC, 0.78% odd-chain FALC, 1.28 mg KOH/g sample of FFA, 13.71 mg KOH/g sample FFE, 2061 ppm carbonyl-containing compounds, and 2.99% moisture. A total of 1.47 wt % NaOH (with an excess of 0.4 wt % NaOH) was added to the starting material at 130° C. and 360 torr and stirred for 2 hours to go through the neutralization and saponification process to obtain a first mixture. The first mixture (distillate of neutralized/saponified FALC) included an intermediate FALC where FFA and FFE impurities (meeting detergent or chemical feed stock specifications) were removed via evaporation. Herein, the first mixture was evaporated at 240° C. of evaporation bottom temperature and 2 torr to generate a second mixture enriched for FALC. The composition of the second mixture is shown in Table 14 below. Notably, the composition of the second mixture included FALC of about 98.5% purity. The high purity of the enriched FALC mixture was surprising because it is achieved by a relatively simple two-step procedure (i.e., saponification and evaporation (SAP/EVAP)). The 98.5% pure FALC still contained minute quantities of some impurities such as 600 ppm carbonyl and 7.8 ppm sulfur. These impurities are so small that they do not interfere with using the 98.5% FALC for commercial products. However, any left-over impurities can be removed via bleaching, polishing and fractional distillation. In addition, unsaturation of FALC can be reduced through a subsequent hydrogenation step.

To test the removal of small impurities, the following conditions were used for bleaching at 115° C. at 80 torr for 1 hour of reaction time using 0.5 wt % F-160 (BASF) bleaching clay. A one-pot batch slurry hydrogenation step was employed to reduce unsaturated FALC at 130° C., 450 psi H2, 4 hours of reaction time using 1.5% active nickel (PRICAT™ 9910 from Johnson Matthey). After bleaching and hydrogenating the purity of the FALC increased to about 98.8%. To demonstrate quality of mid-cut FALC (MC-FALC) generated through the new process steps of the current invention, light fraction (LC-FALC) was first removed at 83° C. of vapor temperature and 2 torr with 2:1 reflux ratio followed by distillation of MC-FALC at 168° C. of vapor temperature and 2 torr with 2:1 reflux ratio. Although chain-length distribution of MC-FALC generated is not exactly meeting the commercial MC-FALC, it is close enough to demonstrate all other specifications except hydroxyl value.

TABLE 14

| | UNIT | Crude FALC | SE-FALC | BF-FALC | HF-FALC | MC-FALC | LC-FALC | MC-FALC Specification |
|---|---|---|---|---|---|---|---|---|
| FALC Purity | % | 90.73 | 98.57 | 97.82 | 98.81 | 99.29 | 96.11 | >98.9 |
| Odd-chain FALC | % | 0.78 | 1.04 | 1.09 | 1.67 | 1.89 | 1.91 | |
| Even-chain FALC | % | 89.95 | 97.53 | 96.73 | 94.44 | 97.4 | 94.2 | |
| Acid Number | mg KOH/g | 1.28 | ND | ND | ND | ND | ND | 0.1 |
| SAP | mg KOH/g | 13.71 | 0.35 | 0.38 | 0.1 | 0.33 | 0.33 | 0.5 |
| Carbonyls | ppm | 2061 | 600 | 570 | 119 | 48 | 23 | 150 |
| Antifoam | % | N/A | N/A | N/A | N/A | N/A | N/A | N/A |
| Moisture | ppm | 29,900 | 500 | 1,900 | 3,900 | 400 | 400 | 1,000 |
| Metals | | | | | | | | |
| Silicon (Si) | ppm | N/A | N/A | N/A | N/A | N/A | N/A | N/A |
| Sulfur (S) | ppm | 230 | 7.8 | 2.7 | <1 | <1 | <1 | <1 |
| Sodium (Na) | ppm | | <1 | <1 | <1 | <1 | <1 | <1 |
| Iodine Value (IV) | | 69.3 | 71 | 72 | 0.1 | 0.28 | 0.28 | 0.3 |
| Hydrocarbon | % | ND | ND | ND | 0.06 | ND | 0.86 | <1 |
| APHA Color | | brown | N/A | N/A | <5 | <5 | <5 | 10 |
| Even-chain FALC composition | % | 100 | 100 | 100 | 100 | 100 | 100 | 100 |
| $C_6OH:0$ | % | 1.09 | 1.12 | 1.08 | 1.08 | 0.03 | 9.35 | 0.0 |
| $C_8OH:0$ | % | 5.61 | 6.08 | 6.03 | 6.05 | 1.58 | 43.0 | 0.3 |
| $C_{10}OH:0$ | % | 11.66 | 12.08 | 12.08 | 13.72 | 11.82 | 30.71 | 1.0 |
| $C_{10}OH:1$ | % | 1.43 | 1.50 | 1.49 | 0.0 | 0.0 | 0.0 | 0.0 |
| $C_{12}OH:0$ | % | 18.48 | 19.14 | 19.15 | 57.22 | 62.6 | 16.29 | >65 |
| $C_{12}OH:1$ | % | 38.14 | 39.49 | 39.5 | 0.14 | 0.15 | 0.06 | 0.0 |
| $C_{14}OH:0$ | % | 7.79 | 7.40 | 7.45 | 13.16 | 14.76 | 0.51 | 21-28 |
| $C_{14}OH:1$ | % | 6.45 | 6.17 | 6.18 | 0.0 | 0.0 | 0.0 | 0.0 |
| $C_{16}OH:0$ | % | 0.68 | 0.49 | 0.49 | 6.47 | 7.28 | 0.07 | 4-8 |
| $C_{16}OH:1$ | % | 7.22 | 5.67 | 5.67 | 0.03 | 0.03 | 0.0 | 0 |
| $C_{18}OH:0$ | % | 0.0 | 0.0 | 0.0 | 2.13 | 1.81 | 0.0 | 0.5 |
| $C_{18}OH:1$ | % | 1.45 | 0.87 | 0.88 | 0.0 | 0.0 | 0.0 | 0.0 |
| $C_{12}OH/C_{14}OH$ | | | | | | 4.3 | | 2.5-3.1 |
| $C_{12}OH + C_{14}OH$ | % | | | | | 77.3 | | 86-93 |

As is apparent to one with skill in the art, various modifications and variations of the above aspects and embodiments can be made without departing from the spirit and scope of this disclosure. Such modifications and variations are within the scope of this disclosure.

We claim:

1. A method of purifying a fatty alcohol (FALC), comprising:
   (a) providing a starting material comprising FALC and saponifiable impurities,
   wherein said saponifiable impurities comprise free fatty acid (FFA), fatty-fatty ester (FFE), and carbonyl-containing compounds;
   wherein the starting material comprises (a) at least 0.1 to 0.5 weight percent FFA or (b) at least 0.1 to 0.5 weight percent FFE; and
   wherein the starting material is a fatty alcohol composition produced by a recombinant *E. coli* host cell grown in a fermentation broth;
   (b) adding a strong base comprising 0.3 to 0.6 weight percent sodium hydroxide (NaOH) to said starting material to generate a first mixture; and
   (c) evaporating FALC from said first mixture to generate a second mixture enriched for FALC, wherein the FALC in the second mixture is about 98% pure.

2. The method of claim 1, wherein said strong base:
   (a) reduces the FFA and the FFE by neutralizing the FFA and saponifying the FFE, wherein saponifying the FFE generates additional FFA for neutralization and additional FALC, and wherein said strong base further reduces the carbonyl-containing compounds.

3. The method of claim 2, wherein said neutralizing and saponifying is carried out at a temperature of about 100° C. to about 130° C., at ambient pressure to partial vacuum of about 80 torr.

4. The method of claim 3, wherein said neutralizing and saponifying is carried out for about 2 to 4 hours.

5. The method of claim 1, wherein an amount of FFA in said second mixture is less than about 0.03 mg KOH/g sample and an amount of FFE in said second mixture is less than about 0.4 mg KOH/g sample.

6. The method of claim 1, wherein an amount of sodium soap in said second mixture is less than about 20 ppm.

7. The method of claim 1, further comprising bleaching the second mixture with a bleaching agent to generate bleached FALC.

8. The method of claim 7, wherein the bleaching agent is selected from the group consisting of a hypochlorite, a peroxide, a bleaching clay, and an absorbent.

9. The method of claim 8, wherein said bleaching agent removes metallic compounds; color bodies; and trace levels of impurities.

10. A method of generating a hydrogenated fatty alcohol (FALC), comprising:
   (a) providing a starting material comprising FALC and saponifiable impurities,
      wherein said saponifiable impurities comprise free fatty acid (FFA), fatty-fatty ester (FFE), and carbonyl-containing compounds;
      wherein the starting material comprises (a) at least 0.1 to 0.5 weight percent FFA or (b) at least 0.1 to 0.5 weight percent FFE; and
      wherein the starting material is a fatty alcohol composition produced by a recombinant *E. coli* host cell grown in a fermentation broth;
   (b) adding a strong base comprising 0.3 to 0.6 weight percent sodium hydroxide (NaOH) to said starting material to generate a first mixture;
   (c) evaporating FALC from said first mixture to generate a second mixture enriched for FALC, wherein the FALC in the second mixture is about 98% pure; and
   (d) hydrogenating the second mixture with hydrogen and a catalyst to generate hydrogenated FALC.

11. The method of claim 10, wherein said hydrogenating is selected from the group consisting of a one pot slurry reaction, a slurry reaction followed by a packed bed reaction, and two packed bed reactions in series.

12. The method of claim 10, further comprising fractionating the hydrogenated FALC according to boiling point, wherein FALC having a difference in chain length of two or more carbons are separated.

13. The method of claim 10, wherein the hydrogenated FALC comprises at least about 50 percent C12 to C18 fatty alcohol.

14. The method of claim 1, wherein the starting material comprises:
   (a) at least 0.1 to 0.5 weight percent of said carbonyl-containing compounds; or
   (b) less than 1 weight percent dialcohol compounds; or
   (c) sulfur or at least one sulfur-containing compound; or water.

15. The method of claim 3, wherein the starting material comprises a saponification (SAP) value of about 20 mg KOH/g or less.

16. The method of claim 1, wherein said evaporating is conducted at a temperature:
   (a) of less than about 150° C. at about 1 torr; or
   (b) of less than about 187° C. at about 5 torr; or
   (c) that corresponds to a vapor pressure of a $C_{18}$ alcohol.

* * * * *